(12) United States Patent
Mikkelsen et al.

(10) Patent No.: US 8,086,081 B2
(45) Date of Patent: Dec. 27, 2011

(54) OPTICAL SUBASSEMBLY FOR IN-AND/OR OUT-COUPLING OF ELECTROMAGNETIC RADIATION INTO, AND/OR OUT OF, A PRESSURE-TIGHT HOUSING

(75) Inventors: Hakon Mikkelsen, Aldenhoven (DE);
Andreas Muller, Ostfilden (DE);
Martin Hertel, Steinen (DE)

(73) Assignee: Endress + Hauser Conducta Gesellschaft für Mess-und Regeltechnik mbH + Co. KG, Gerlingen (DE)

( * ) Notice: Subject to any disclaimer, the term of this patent is extended or adjusted under 35 U.S.C. 154(b) by 44 days.

(21) Appl. No.: 12/379,391

(22) Filed: Feb. 20, 2009

(65) Prior Publication Data
US 2009/0285526 A1 Nov. 19, 2009

(30) Foreign Application Priority Data
Feb. 20, 2008 (DE) .......................... 10 2008 010 207

(51) Int. Cl.
*G02B 6/26* (2006.01)
*G02B 6/42* (2006.01)
*G02B 6/00* (2006.01)
(52) U.S. Cl. .......................... 385/31; 385/135
(58) Field of Classification Search .................. None
See application file for complete search history.

(56) References Cited

U.S. PATENT DOCUMENTS
| 4,265,303 | A  | * | 5/1981 | Giurtino et al. | ............... 165/166 |
| 6,764,226 | B1 | * | 7/2004 | Freeman et al. | ................. 385/88 |
| 2007/0003207 | A1 | * | 1/2007 | Dunphy et al. | ............... 385/138 |

FOREIGN PATENT DOCUMENTS
| DE | 43 17 931 A1 | 12/1994 |
| DE | 201 10 274 U1 | 9/2002 |
| DE | 20 2006 014 464 U1 | 1/2007 |
| DE | 600 33 412 T2 | 11/2007 |

\* cited by examiner

*Primary Examiner* — Tina Wong
(74) *Attorney, Agent, or Firm* — Bacon & Thomas, PLLC

(57) ABSTRACT

An optical subassembly for in- and/or out-coupling of electromagnetic radiation of a predetermined wavelength, especially IR-radiation, into, and/or out of, a pressure-tight housing. The subassembly includes at least one housing wall section of the pressure-tight housing having at least one opening, wherein, in the opening, mechanical setting means are provided, with which a plug transparent for the electromagnetic radiation is set, wherein the transparent plug has two mutually oppositely lying, base surfaces and a cylindrical lateral surface, and wherein the setting means include as least one setting ring, characterized in the a volume region between at least a first section of the setting ring and at least a section of the cylindrical lateral surface is filled with a pressure-tight, potting compound.

16 Claims, 3 Drawing Sheets

OPTICAL SUBASSEMBLY FOR IN-AND/OR OUT-COUPLING OF ELECTROMAGNETIC RADIATION INTO, AND/OR OUT OF, A PRESSURE-TIGHT HOUSING

TECHNICAL FIELD

The invention relates to an optical subassembly for in- and/or out-coupling of electromagnetic radiation of a predetermined wavelength range, especially IR-radiation, especially in the wavelength range of 4 to 15 µm, into, and/or out of, a pressure-tight housing.

BACKGROUND DISCUSSION

Such an optical subassembly is required, for example, for optical sensors or communication devices, in the case of which a receiver sensitive for electromagnetic radiation and/or a transmitter transmitting electromagnetic radiation are/is accommodated in a housing. For the interaction of the transmitter, or receiver, as the case may be, with the environment outside of the housing, it is necessary to couple electromagnetic radiation into, or out of, the housing. An optical sensor for performing absorption measurements or measurements of attenuated total reflectance, so-called ATR-measurements, can be so embodied, that a radiation source and a spectrometer are accommodated in a housing, while a probe for immersion into a process medium outside of the housing is connected via optical fibers with the radiation source and with the spectrometer. In this case, in the measuring, electromagnetic radiation of the radiation source is coupled out of the housing, brought via the optical fibers into the probe, there reflected, and then coupled via optical fibers back into the housing, where it falls on the detector of the spectrometer. German Gebrauchsmuster DE 295 21 685 U1 discloses an optical component, intended especially for an infrared radiator, having a housing, which has an opening closed by means of an optical window or lens of sapphire for radiation entering, or leaving, the housing, wherein, between the edge of the opening and the window or lens, an encircling, metal solder connection is provided. This optical component seals the housing vacuum-tightly.

German Gebrauchsmuster DE 20 2006 014 464 U1 discloses a sensor arrangement, in the case of which electromagnetic radiation can be coupled into, or out of, a housing, through a housing opening. For this, there is provided in the housing an opening, which is covered with a window transmissive for the electromagnetic radiation. The window is pressed against the housing at its edge, with interpositioning of a seal. This tightly seals the housing, even under demanding conditions, such as a liquid pressure of up to 100 bar and a temperature of up to 50° C.

DE 102 46 762 A1 shows a communication window for a pressure-tight housing having an opening in a housing wall. The opening is embodied as an optically transparent, elongated window pane and is arranged within a sleeve-shaped, screw-threaded frame, which can be pressure-tightly screwed into the opening.

SUMMARY OF THE INVENTION

An object of the present invention is to provide an optical subassembly for the in- and/or out-coupling of electromagnetic radiation into, and/or out of, a housing, which is explosion-protected and meets especially the requirements of the Ex-protection permit "Ex-d" (pressure-tight encapsulation). This means that, in case of an internal explosion, the pressure-tight housing must not be damaged and that, especially, an escape of the explosion beyond the housing wall out into the environment must be suppressed. A housing, which satisfies these requirements is referenced here and in the following as a pressure-tight housing.

The standards pertinent for the Ex protection permit Ex-d are EN 50079 and EN 60079. Standards comparable with these European standards exist in the USA, Canada, Japan and other countries.

The above object of the invention is achieved by an optical subassembly for in- and/or out-coupling of electromagnetic radiation of a predetermined wavelength range into, and/or out of, a pressure-tight housing, wherein the optical subassembly comprises at least a housing wall section of the pressure-tight housing, which has at least one opening, has, in the opening, mechanical setting means, with which a plug transparent for the electromagnetic radiation is held, wherein the transparent plug has two oppositely lying, base surfaces and a cylindrical lateral surface, and wherein the setting means comprises at least one setting ring, wherein a volume region between at least a first section of the setting ring and at least a part of the cylindrical lateral surface is filled with a pressure-tight, potting compound.

Such a mechanical setting of the transparent plug, secured supplementally by casting, assures, compared with the mechanical pressing via a sealing ring, such as described in DE 20 2006 014 464 U1, an increased explosion safety. While a conventional sealing ring would be destroyed in the case of an explosion accompanied by rapid temperature and pressure rise, there can be selected for casting a potting compound permitted in the explosion standards that can withstand these extreme conditions. For achieving sufficient explosion protection, it is furthermore necessary, that there be no crack formation in the transparent plug or development of a gap between the cylindrical lateral surface of the transparent plug and the setting means. Such a crack or gap represents, at the same time, a leak for the pressure-tight housing. If the pressure-tight housing contains, for example, a radiation source and a spectrometer for executing absorption- or ATR-measurements, the transparent plug and the setting means can be subjected to a temperature range between 20 and 60° C. In such a broad temperature range, there is already a significant material expansion. The stresses arising in such case due to the differing coefficients of expansion of the individual components can lead to crack, or gap, formation. Also mechanical shocks can lead to cracks. Compared with the screwing of the transparent plug into the housing wall, such as is described in DE 102 46 762, casting has the advantage that stresses in the radial direction are reduced, or shocks damped, by the cast potting-compound. In this way, the danger of a crack- or gap-formation is lessened compared to the screwed connection into the housing wall known from the state of the art, since such screwed connection is not resilient in the radial direction.

The term, "radial", means here, and in the following, the direction perpendicular to the optical axis of the optical subassembly. The direction parallel to the optical axis is then referred to with the label, "axial".

In a further embodiment, the volume region between the first section of the setting ring and the cylindrical lateral surface filled with the potting compound has in the axial direction a length of at least 10 mm. In the radial direction, the thickness of the cast material measures at least 3 mm.

In a preferred further development, the setting ring includes a second section, which is connected with a ferrule for receiving at least one optical fiber in such a manner that radiation leaving the optical fiber falls on the base surface of the transparent plug facing the optical fiber, or such that radiation leaving the base surface facing the optical fiber is focused on the in-coupling surface of the optical fiber. Such an arrangement assures that radiation leaving the housing is coupled into the optical fiber with as little radiation loss as possible, or that the radiation leaving the fiber is correspondingly coupled into the housing with as little loss as possible and can be received by a receiver arranged in the housing.

In a further form of embodiment, the housing wall section forms simultaneously the wall of another, second housing following directly on the pressure-tight housing. The second housing encloses at least the second section of the setting ring with the ferrule and at least a section of the optical fiber secured in the ferrule. Such a further housing serves for protecting the sensitive optical fibers from mechanical or chemical damage or from damage by incoming light, e.g. from sun light.

In a further development of this form of embodiment, the second housing tapers with increasing distance from the housing wall section of the pressure-tight housing and has on its end opposite to the housing wall section a seat for a sensor tube.

The sensor tube can serve as seating for the at least one optical fiber. In this way, the optical fiber is yet better affixed in the second housing and the danger of mechanical damage is lessened.

In a further development of this form of embodiment, also the second housing is cast full with a potting compound. The casting full of also this further housing serves for supplemental sealing of the pressure-tight housing and improves explosion safety.

In such case, it is advantageous, when the second section of the setting ring protrudes with the potting compound with an axial length of at least 10 mm into the second housing. With such a casting length, the requirements of the cited explosion protection standards, especially the standards relevant for encapsulation with potting compound, are fulfilled.

For mechanical securement of the setting ring in the opening, a threaded pin extending radially in the housing wall section can be provided. A securement of such type is structurally simple, since no further setting components are required, and, in the assembly of the optical subassembly before the casting, also capable of being easily released again.

The base surfaces of the transparent plug can be planar, or, in a preferred form of embodiment, convexly curved. Making the base surfaces convex permits focusing, onto the optical fiber, of a light ray diverging from a light source. In this way, light losses can be minimized. The transparent plug acts in this case as a lens, more accurately, as a collecting lens. If the base surfaces of the transparent plug are planar, then it acts only as a window. Also an embodying of the transparent plug as a Fresnel lens is possible.

In a further embodiment, the setting means comprise, besides the setting ring, on the side facing away from the pressure-tight housing, a cylindrical aperture boundary, especially in the form of a projection of the setting ring, as bearing location for the transparent plug. The projection serves simultaneously as an axial stop for the plug and cares, thus, for correct axial positioning of the plug.

Furthermore, the setting means can include, on the side facing the pressure-tight housing, a leading screw ring, which serves for affixing the transparent plug in the axial direction. The thread gap of the leading screw ring is dimensioned in accordance with the above-cited standards for a pressure-tight housing. The optical axis is defined, in the case of embodying the transparent plug as a collecting lens, i.e. with two convex base surfaces, by the optical axis of the transparent plug. In case the transparent plug is embodied as a plan-parallel plate, thus with two planar, base surfaces, then the optical axis is the axis of symmetry of the rotationally symmetric, transparent plug.

In a preferred embodiment, the optical fiber is connected with a probe, for example with a transmission cell or an ATR-probe, especially for performing measurements in liquids.

In a further embodiment, the transparent plug is made of ZnSe, Ge, diamond or sapphire. These materials are transparent for infrared radiation and are thus especially suited for use in optical sensors working in this wavelength range.

In order to assure a sufficient explosion safety, it is advantageous, when the potting compound possesses a UL-certification, i.e. the standards specified by the US organization, Underwriters Laboratories, Inc., for potting compounds for explosion protection. Such a potting compound can be composed, for example, of two components, wherein the first component can be an epoxide resin with an inorganic filler material and the second component a hardener based on polyamine. A pressure-tight housing, which is explosion-protected and, especially, meets the above-cited standards, includes at least one optical subassembly for in- and out-coupling of electromagnetic radiation according to one of the aforementioned embodiments. Preferably, such a pressure-tight housing is used for accommodating a light source and/or a detector, especially a spectrometer in an optical sensor, for example for absorption- or ATR-measurements.

In an embodiment, the optical subassembly with the housing wall section, in which the described opening is provided for in- and out-coupling of electromagnetic radiation, is secured by means of a union nut to at least one other housing module, so that the optical subassembly encloses together with the housing module a pressure-tightly sealed space. Also thread gap and sealing of the union nut are so chosen that they meet the relevant explosion standards.

In a special further development of this embodiment, the optical subassembly forms with the housing wall section, in which the transparent plug is set and with the second housing adjoining the pressure-tight housing, a pressure tight (thus conforming to the explosion protection standards), double-walled covering for the pressure-tight housing. In this case, it is advantageous to provide only one additional housing module. The optical subassembly is then secured by means of the union nut to the other housing module as a double-walled "lid" (compare also FIG. 3), so that a pressure-tightly closed space results.

BRIEF DESCRIPTION OF THE DRAWINGS

The invention will now be explained on the basis of an example of an embodiment shown in the drawing, the figures of which show as follows.

DETAILED DISCUSSION

Figure 1:
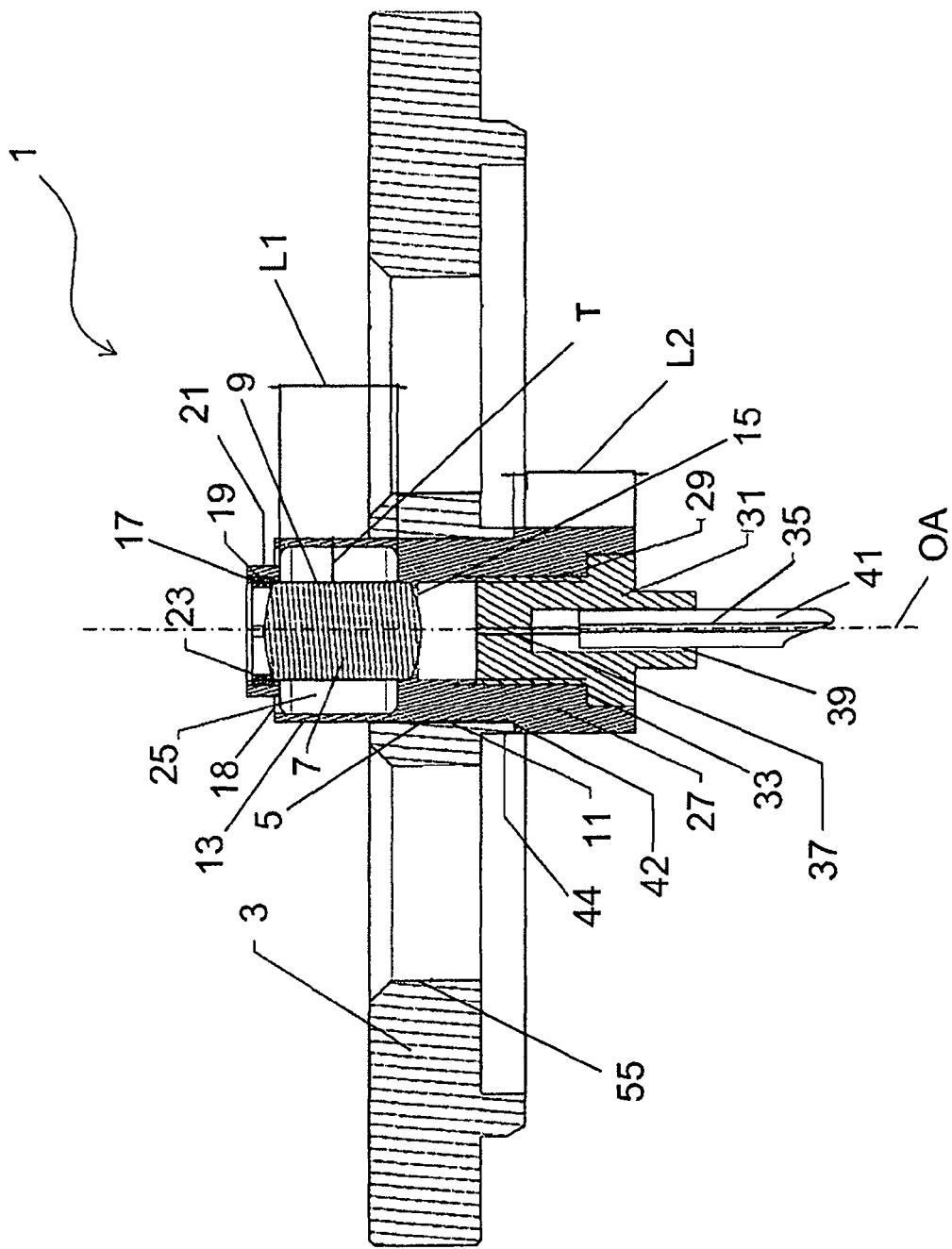
FIG. 1 a schematic sketch of the optical subassembly.

FIG. 1 shows an optical subassembly 1 for in- and/or out-coupling of electromagnetic radiation into, and/or out of, a pressure-tight housing. In the housing wall section 3 of the pressure-tight housing is an opening 5. The opening 5 permits the passage of electromagnetic radiation, which can either be coupled from a radiation source arranged in the pressure-tight housing into a probe attached outside of the housing, or, the other way around, from the probe back into the housing, where it falls on a detector of a spectrometer likewise arranged in the pressure-tight housing.

Arranged in the opening 5, in a setting ring 11, is a bi-convex, collecting lens 7 having a surrounding, lens-side surface 9, which is embodied as a cylindrical lateral surface. Bi-convex, collecting lens 7 is provided in the form of a plug of material transmissive for the electromagnetic radiation. When infrared radiation is used, especially radiation in a wavelength range of 4 to 15 µm, suitable transparent materials include, for example, zinc selenide (ZnSe), germanium (Ge), sapphire ($Al_2O_3$) or diamond.

Setting ring 11 includes a plurality of sections of different wall thickness. A first setting ring section 13 is arranged around the lens side surface 9, with the inner wall of this setting ring section 13 extending around the lens side surface 9 of the collecting lens 7 essentially spaced therefrom at constant radial separation D. An aperture border 15, which is provided in the form of a projection of the setting ring 11, serves to provide an axial stop for the collecting lens 8 on the side facing away from the housing interior. Serving on the side of the collecting lens 7 opposite to the aperture border 15 for axial affixing of the collecting lens 7 is an externally threaded ring 17. The externally threaded ring 17 is screwed via a thread 19 into a second section 21 of the setting ring 11 stepped radially inwards in the direction toward the optical axis OA.

The externally threaded ring 17 can be supplementally secured with a fast-drying, screw-setting adhesive 23. Such adhesives based on epoxide resin, or fast-drying, cyano-acry-late, thread adhesives, are known to those skilled in the art.

Setting ring 11, with the first section 13, the stepped, second section 21, and the aperture border 15, forms, together with the lens side surface 9, an intermediate space, in which a potting compound 25 is situated. Potting compound 25 is, ideally, injection cast in such a manner that it fills the intermediate space without bubble formation. For the injecting of the potting compound 25 into the intermediate space, passageways 18 are provided in the setting ring. These passageways 18 are located in the terminal, annular surface formed by the radial step of the second section 21 of the setting ring. The potting compound length L1 and the potting compound thickness T are so selected that they at least equal the length and thickness specified by the European explosion protection standard EN 60079. Comparable standards exist in other countries, such as USA, Japan or Canada. For example, in EN60079, for a volume of the pressure-tight housing of more than 100 $cm^3$, a potting compound length of at least 10 mm is required. Furthermore, a potting compound thickness T of at least 3 mm is specified. Suitable potting compounds according to the cited standards include UL-certified potting compounds, for example two-component systems with the first component being an epoxide resin containing an inorganic filler and a second component being a polyamine-based hardener.

On the side of the aperture border 15 facing away from the collecting lens 7, setting ring 11 includes a third section 27. Section 27 has, internally, a thread 29, into which a ferrule 31 is screwed until contact with an axial stop 33. Ferrule 31 serves for positioning an optical fiber 35 coming from a probe or a fiber bundle coming from the probe, with respect to the collecting lens 7. The axial stop 33 is provided as a radial projection from the lateral surface of the ferrule 31. Ferrule 31 contains in its side facing toward the collecting lens 7 a central passageway 37 for positioning the optical fiber 35, or fiber bundle, as the case may be. Fiber 35, or the fiber bundle, can be secured by adhesive in the bore 37, for example with an epoxide resin-based adhesive or a fast-drying cyano-acrylate-based adhesive.

Optical fiber 35 is made of a material transparent for the electromagnetic radiation. In the case of use of infrared radiation, especially in the wavelength range of 4 to 15 µm, fiber 35 can be made of silver halide. Ferrule 31 is made of a mechanically sufficiently form-stable material, which is chemically compatible with the silver halide of the fiber 35, especially a plastic, or synthetic material, for example PEEK, or a metal, for example Ag, Au or Ti.

Ferrule 31 is positioned with respect to the collecting lens 7 in such a manner that radiation leaving the collecting lens 7 is focused on the end surface of the optical fiber 35 facing the convex lens surface, or such that radiation leaving the corresponding end surface of the optical fiber 35 is collected essentially completely by the collecting lens 7, with as little radiation loss as possible. In the radial direction, this positioning is accomplished by the screwing of the ferrule 31 into connection with the section 27 of the setting ring 11. Axial positioning is accomplished via the axial stop 33 of the ferrule 31.

Ferrule 31 includes, additionally, a central bore 39, which is terminated short of passing completely through the ferrule and which enters from the ferrule end facing away from the pressure-tight housing, and the optical fiber 35 coming from the probe is guided through the bore 39 to the bore 37. Toward the probe, the optical fiber 35 extends through a guide tube 41, which can be made of the same material as the ferrule 31, especially PEEK. Guide tube 41 serves for guiding and simultaneously for protecting the sensitive optical fiber 35 from mechanical loadings, which could lead to damaging of the fiber 35.

Setting ring 11 is held in the housing wall section 3 by a threaded pin (not shown) extending radially within the housing wall section 3. This type of securement permits a structurally simple yet sufficient affixing of the setting ring in the housing wall section 3. If desired, this affixing can be released with simple means. The axial positioning of the setting ring 11 in the housing wall section 3 is accomplished via an axial stop 42, which can be formed as a radial projection on the setting ring 11, which engages in an annular projection 44 of the housing section 3. The setting ring 11 can be manufactured of a suitable, corrosion-resistant steel, such as, for example, VA 1.4371.

Figure 2:
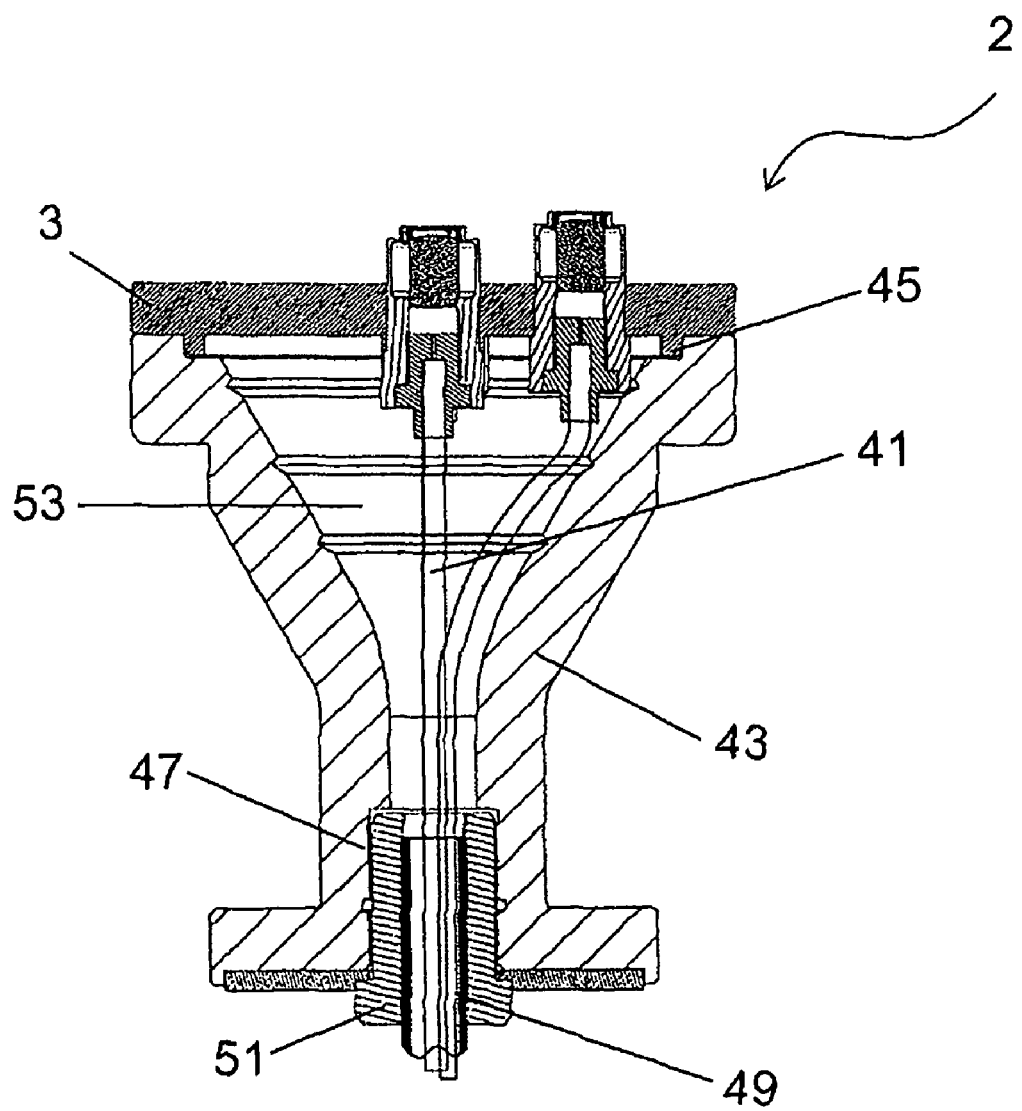
FIG. 2 a schematic sketch of the optical subassembly with an additional housing surrounding the optical fibers.

As a further explosion protection measure, an additional housing can adjoin the housing wall section 3 of the pressure-tight housing for reception of the optical fiber 35. This additional housing is likewise filled with potting compound 25. An optical subassembly 2 with such an additional housing is illustrated in FIG. 2.

The additional housing is provided here in the form of a funnel 43, which is connected with the housing wall section 3 by means of three axial screws (not shown) and which engages an annular projection 45 of the housing wall section 3. Funnel 43 tapers with increasing separation from the housing wall section 3. On the end of funnel 43 opposite to the housing wall section 3, there is provided, in the neck of the funnel, a cylindrical bore 47, which serves for accommodating a probe tube 49. Probe tube 49 is screwed into a seat 51. Supplementally or alternatively, the probe tube 49 can also be held in the seat 51 with a retaining ring. Seat 51 is secured in the cylindrical bore 47 by means of two set-screws (not shown). Seat 51 serves for positioning the probe tube 49 relative to the optical fiber 35 guided from the ferrule 31 in the guide tube 41. Probe tube 49 and seat 51 are designed such that also a plurality of guide tubes can be contained therein. In this way, it is possible to provide a plurality of optical subassemblies in the housing wall section 3, through which radiation can be coupled into, or out of, the pressure-tight housing. For example, FIG. 2 shows two such subassemblies.

The funnel interior 53 is filled with a potting compound 25 acceptable according to the cited explosion protection standards. Such potting compound improves explosion safety, especially with respect to the connecting location between the setting ring 11 and the housing wall section 3, which, without the potting compound, is formed in the housing wall section 3 only by means of the threaded pin (not shown) extending in the housing wall section 3. In order to fulfill the requirements for explosion protection, the potting compound length L2 (see FIG. 1), which is the distance between the axial stop 42 of the setting ring 11 and the end of the setting ring 11 facing away from the housing wall section 3, is chosen, according to the explosion protection standards, especially to be at least 10 mm in the case of a housing size of more than 100 cm$^3$.

Provided in the housing wall section 3 are one or more passageways 55, which serve for injection of the potting compound 25 into the funnel 43 (FIG. 1).

FIG. 2 shows two transparent plugs, and their setting means, provided in a housing wall section 3 for in- and/or out-coupling of electromagnetic radiation into, or out of, the pressure-tight housing. Depending on field of application, one or more transparent plugs can be provided. Also, each transparent plug can be coupled with one or more optical fibers 35. The coupling of a plurality of fibers is desirable, for instance, when a plurality of different signals must be transmitted simultaneously, for example, in the case of a simultaneous, fiber-based, temperature measurement supplemental to the recording of an ATR spectrum. Also, in the case of spectroscopic measurements, simultaneously, measurement light and reference light coming directly from the light source without contact with the sample can be transmitted over different fibers.

Figure 3:
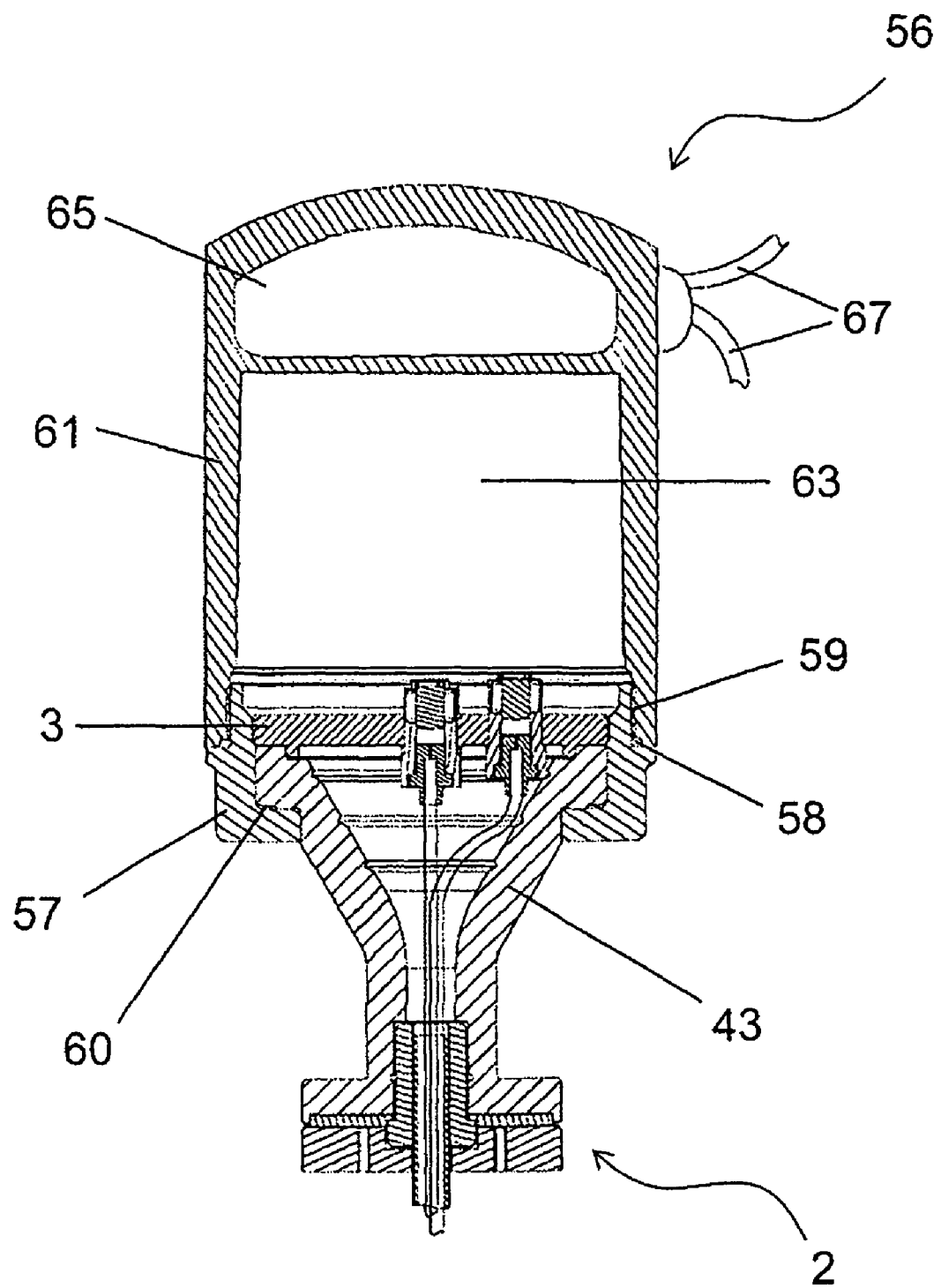
FIG. 3 a schematic sketch of the pressure-tight housing with the optical subassembly for in- and/or out-coupling of electromagnetic radiation into, and/or out of, the housing.

FIG. 3 shows a pressure-tight housing 56 with the above-described subassembly 2, including a housing wall section 3 with two transparent plugs set therein, as well as an additional housing in the form of a funnel 43. The pressure-tight housing 56 is formed of a housing module 61 and the subassembly 2. The funnel 43 and the housing wall section 3 are secured by means of a coupling nut 57 via the thread 59 on the housing module 61. A sealed closure between the housing module 61 and the coupling nut is assured by an O-ring 58. A seal between the funnel 43 and the coupling nut is obtained by means of a sealing ring 60. The thread gap of the coupling nut 57 is dimensioned according to the above-cited standards for pressure-tight encapsulation.

The subassembly 2 with housing wall section 3 and funnel 43, thus, bring about a pressure-tight, double-walled closure of the housing module 61 and provide the remaining walls of the pressure-tight housing. The housing interior space 63 formed in the way is thus sealed pressure-tightly, so that it forms an explosion-protected accommodation, for example, for a light source and/or a spectrometer for optical measurements.

Affixed in the housing module 61 is, additionally, a base-plate (not shown), on which a spectrometer, for example, can be constructed and affixed. Simultaneously, the base-plate prevents, in the case of an explosion, that the subassembly 2 with the housing wall section 3 and the funnel 43 are pressed into the housing.

Housing module 61 includes an additional, adjoining space 65 separated from the interior 63. Space 65 serves for accommodating electrical lines. Space 65 is so embodied that it meets the requirements of the explosion protection permit "Ex-e". The electrical supply of the components located in the housing interior 63 is accomplished by means of electrical connections 67 via feedthroughs (not shown) in the outer wall of the pressure-tight housing 56. The lines in the adjoining space are connected with the components located in the housing interior 63 by means of conventional cable-feedthroughs according to Ex-d- and Ex-e-protection permits.

The invention claimed is:

1. An optical subassembly for in- and/or out-coupling of electromagnetic radiation of a predetermined wavelength range, especially IR-radiation, into, and/or out of, a pressure-tight housing, comprising:
    at least one housing wall section of the pressure-tight housing, said at least one housing wall section has at least one opening; and
    mechanical setting means in said at least one opening for setting a transparent plug for the electromagnetic radiation, said transparent plug includes two oppositely lying, base surfaces and a cylindrical lateral surface, and said mechanical setting means includes at least one setting ring, wherein:
    a volume region between at least a first section of said setting ring and at least a section of said cylindrical lateral surface is filled with a pressure-tight potting compound;
    said setting ring includes a second section, which is connected in such a manner with a ferule for accommodating at least one optical fiber, that radiation leaving the optical fiber falls on a base surface of said transparent plug facing the optical fiber;
    said at least one housing wall section forms a wall of a second housing adjoining the pressure-tight housing, and the second housing encloses at least said second section of said setting ring with said ferule and at least a section of the optical fiber secured in said ferule;
    said second housing tapers with increasing distance from said housing wall section of the pressure-tight housing and possesses at its end opposite said housing wall section a seat for a sensor tube.

2. The optical subassembly as claimed in claim 1, wherein:
    said volume region filled with the potting compound between said first section of said setting ring and said cylindrical lateral surface has an axial length of at least 10 mm and a radial thickness of at least 3 mm.

3. The optical subassembly as claimed in claim 1, wherein:
    said sensor tube serves as a receptacle for said at least one optical fiber.

4. The optical subassembly as claimed in claim 1, wherein:
    said second housing is filled out with potting compound.

5. The optical subassembly as claimed in claim 4, wherein:
    said second section of said setting ring protrudes with a length of at least 10 mm into said second housing filled with the potting compound.

6. The optical subassembly as claimed in claim 1, wherein:
    said base surfaces of said transparent plug are planar surfaces or convexly curved surface.

7. The optical subassembly as claimed in claim 1, wherein:
    said setting ring further includes on its end facing away from said pressure-tight housing a cylindrical aperture border, especially in the form of a radial projection of said setting ring, as a bearing location for said transparent plug.

8. The optical subassembly as claimed in claim 1, wherein:
    said mechanical setting means further includes an externally threaded ring screwed onto said setting ring on its end facing said pressure-tight housing for axially affixing said transparent plug.

9. A pressure-tight housing, comprising:
at least one housing wall section with at least one optical subassembly for in- and out-coupling of electromagnetic radiation, said optical subassembly comprising:
at least one housing wall section of the pressure-tight housing, said at least one housing wall section has at least one opening; and
mechanical setting means in said at least one opening for setting a transparent plug for the electromagnetic radiation, said transparent plug includes two oppositely lying, base surfaces and a cylindrical lateral surface, and said mechanical setting means includes at least one setting ring, wherein:
a volume region between at least a first section of said setting ring and at least a section of said cylindrical lateral surface is filled with a pressure-tight potting compound;
said setting ring includes a second section, which is connected in such a manner with a ferule for accommodating at least one optical fiber, that radiation leaving the optical fiber falls on a base surface of said transparent plug facing the optical fiber;
said at least one housing wall section forms a wall of a second housing adjoining the pressure-tight housing, and the second housing encloses at least said second section of said setting ring with said ferrule and at least a section of the optical fiber secured in said ferrule; and
said second housing tapers with increasing distance from said housing wall section of the pressure-tight housing and possesses at its end opposite said housing wall section a seat for a sensor tube.

10. The pressure-tight housing as claimed in claim 9, wherein:
said optical subassembly is secured to another housing module by means of a coupling nut, so that the optical subassembly encloses together with said housing module a pressure-tightly sealed space.

11. The optical subassembly of claim 9, wherein:
said setting ring is affixed in said housing wall section by means of a threaded pin extending radially in said housing wall section.

12. An optical subassembly for in- and/or out-coupling of electromagnetic radiation of a predetermined wavelength range, especially IR-radiation, into, and/or out of, a pressure-tight housing, comprising:
at least one housing wall section of the pressure-tight housing, said at least one housing wall section has at least one opening; and
mechanical setting means in said at least one opening for setting a transparent plug for the electromagnetic radiation, said transparent plug includes two oppositely lying, base surfaces and a cylindrical lateral surface, and said mechanical setting means includes at least one setting ring, wherein:
a volume region between at least a first section of said setting ring and at least a section of said cylindrical lateral surface is filled with a pressure-tight potting compound;
said setting ring includes a second section, which is connected in such a manner with a ferule for accommodating at least one optical fiber, that radiation leaving the optical fiber falls on a base surface of said transparent plug facing the optical fiber; and
said at least one housing wall section forms a wall of a second housing directly adjoining the pressure tight housing, and the second housing encloses at least said second section of said setting ring with said ferrule and at least a section of the optical fiber secured in said ferrule, wherein said second housing is filled with potting compound.

13. The optical subassembly of claim 12, wherein:
said second section of said setting ring protrudes with a length of at least 10 mm into said second housing filled with the potting compound.

14. An optical subassembly for in- and/or out-coupling of electromagnetic radiation of a predetermined wavelength range, especially IR-radiation, into, and/or out of, a pressure-tight housing, comprising:
at least one housing wall section of the pressure-tight housing, said at least one housing wall section has at least one opening; and
mechanical setting means in said at least one opening for setting a transparent plug for the electromagnetic radiation, said transparent plug includes two oppositely lying, base surfaces and a cylindrical lateral surface, and said mechanical setting means includes at least one setting ring, wherein:
a volume region between at least a first section of said setting ring and at least a section of said cylindrical lateral surface is filled with a pressure-tight potting compound,
said setting ring further includes on its end facing away from said pressure-tight housing a cylindrical aperture border, especially in the form of a radial projection of said setting ring, as a bearing location for said transparent plug;
said setting means further includes an externally threaded ring screwed onto said setting ring on its end facing said pressure-tight housing for axially affixing said transparent plug;
said volume region filled with the potting compound between said first section of said setting ring and said cylindrical lateral surface has an axial length of at least 10 mm and a radial thickness of at least 3 mm;
said setting ring includes a second section, which is connected in such a manner with a ferrule for accommodating at least one optical fiber, that radiation leaving the optical fiber falls on a base surface of said transparent plug facing the optical fiber;
said at last one housing wall section forms a wall of a second housing directly adjoining the pressure-tight housing, and the second housing encloses at least said second section of said setting ring with said ferrule and at least a section of the optical fiber secured in said ferrule; and
said second housing tapers with increasing distance from said housing wall section of the pressure-tight housing and possesses at its end opposite said housing wall section a seat for a sensor tube.

15. The optical subassembly as claimed in claim 14, wherein:
said sensor tube serves as a receptacle for said at least one optical fiber.

16. An optical subassembly for in- and/or out-coupling of electromagnetic radiation of a predetermined wavelength range, especially IR-radiation, into, and/or out of, a pressure-tight housing, comprising:
at least one housing wall section of the pressure-tight housing, said at least one housing wall section has at least one opening; and
mechanical setting means in said at least one opening for setting a transparent plug for the electromagnetic radiation, said transparent plug includes two oppositely lying, base surfaces and a cylindrical lateral surface, and said mechanical setting means includes at least one setting ring, wherein:

a volume region between at least a first section of said setting ring and at least a section of said cylindrical lateral surface is filled with a pressure-tight potting compound, said setting ring further includes on its end facing away from said pressure-tight housing a cylindrical aperture border, especially in the form of a radial projection of said setting ring, as a bearing location for said transparent plug;

said setting means further includes an externally threaded ring screwed onto said setting ring on its end facing said pressure-tight housing for axially affixing said transparent plug, said volume region filled with the potting compound between said first section of said setting ring and said cylindrical lateral surface has an axial length of at least 10 mm and a radial thickness of at least 3 mm, said setting ring includes a second section, which is connected in such a manner with a ferrule for accommodating at least one optical fiber, that radiation leaving the optical fiber falls on a base surface of said transparent plug facing the optical fiber, said at last one housing wall section forms a wall of a second housing directly adjoining the pressure-tight housing, and the second housing encloses at least said second section of said setting ring with said ferrule and at least a section of the optical fiber secured in said ferrule, and said second housing is filled out with potting compound.

* * * * *